United States Patent
Eiland et al.

(10) Patent No.: US 10,220,155 B2
(45) Date of Patent: Mar. 5, 2019

(54) SYRINGE DEVICE WITH A DOSE LIMITING MECHANISM AND AN ADDITIONAL SAFETY MECHANISM

(75) Inventors: Jacob Eiland, Virum (DK); Christian Peter Enggaard, Hillerod (DK); Claus Schmidt Moller, Fredensborg (DK); Tom Hede Markussen, Bagsvaerd (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 11/996,397

(22) PCT Filed: Jul. 17, 2006

(86) PCT No.: PCT/EP2006/007006
§ 371 (c)(1),
(2), (4) Date: Mar. 20, 2008

(87) PCT Pub. No.: WO2007/017053
PCT Pub. Date: Feb. 15, 2007

(65) Prior Publication Data
US 2008/0234634 A1      Sep. 25, 2008

Related U.S. Application Data

(60) Provisional application No. 60/708,211, filed on Aug. 15, 2005.

(30) Foreign Application Priority Data

Jul. 27, 2005   (EP) ..................................... 05016286

(51) Int. Cl.
*A61M 5/315*     (2006.01)
*A61M 5/20*      (2006.01)

(52) U.S. Cl.
CPC .......... *A61M 5/31583* (2013.01); *A61M 5/20* (2013.01); *A61M 5/31553* (2013.01);
(Continued)

(58) Field of Classification Search
CPC ............ A61M 5/3155; A61M 5/31528; A61M 5/31581; A61M 5/31578; A61M 5/31583;
(Continued)

(56) References Cited

U.S. PATENT DOCUMENTS

| | | |
|---|---|---|
| 4,498,904 A | 2/1985 | Turner et al. |
| 4,865,591 A | 9/1989 | Sams |

(Continued)

FOREIGN PATENT DOCUMENTS

| | | |
|---|---|---|
| DE | 20209051 | 4/2003 |
| DE | 69810860 | 11/2003 |

(Continued)

OTHER PUBLICATIONS

Non-Final Office Action issued by the USPTO for U.S. Appl. No. 11/996,409 dated Dec. 31, 2008.
(Continued)

*Primary Examiner* — Bhisma Metha
*Assistant Examiner* — Larry R Wilson
(74) *Attorney, Agent, or Firm* — Wesley Nicolas

(57) ABSTRACT

A syringe device for ejecting a dose of a medicament, the syringe device comprising: a dose limiting mechanism arranged to interact with a dose ejecting mechanism to prevent ejection of a dose exceeding a set dose, and a safety mechanism, which is arranged such with respect to the dose ejecting mechanism that, if the dose limiting mechanism fails, the safety mechanism prevents ejection of a dose exceeding the set dose.

8 Claims, 1 Drawing Sheet

(52) U.S. Cl.
CPC ..... *A61M 5/31541* (2013.01); *A61M 5/31558* (2013.01); *A61M 5/31561* (2013.01); *A61M 5/31573* (2013.01); *A61M 5/31593* (2013.01)

(58) Field of Classification Search
CPC .......... A61M 5/31585; A61M 5/31586; A61M 5/31551; A61M 5/3158; A61M 5/51535; A61M 5/31536; A61M 5/31538; A61M 2005/3154; A61M 5/31541; A61M 5/31543; A61M 5/31563; A61M 5/31558; A61M 5/20; A61M 5/31533; A61M 5/31545; A61M 5/31548; A61M 5/31553; A61M 5/31555; A61M 5/31561; A61M 5/31573; A61M 5/31593
USPC .................. 604/181, 187, 207–211, 218–231
See application file for complete search history.

(56) References Cited

U.S. PATENT DOCUMENTS

| | | | |
|---|---|---|---|
| 4,883,472 A | 11/1989 | Michel | |
| 5,104,380 A | 4/1992 | Holman et al. | |
| 5,921,966 A | 7/1999 | Bendek et al. | |
| 5,938,642 A * | 8/1999 | Burroughs et al. | 604/208 |
| 6,221,046 B1 * | 4/2001 | Burroughs et al. | 604/153 |
| 6,221,053 B1 | 4/2001 | Walters et al. | |
| 6,235,004 B1 | 5/2001 | Steenfeldt-Jensen et al. | |
| 6,248,095 B1 | 6/2001 | Giambattista et al. | |
| 6,569,123 B2 * | 5/2003 | Alchas et al. | 604/192 |
| 6,582,404 B1 | 6/2003 | Klitgaard et al. | |
| 6,585,698 B1 * | 7/2003 | Packman et al. | 604/207 |
| 6,663,602 B2 * | 12/2003 | Møller | 604/211 |
| 6,699,224 B2 | 3/2004 | Kirchhofer et al. | |
| 6,899,699 B2 | 5/2005 | Enggaard | |
| 7,104,972 B2 | 9/2006 | Moller et al. | |
| 7,169,132 B2 | 1/2007 | Bendek et al. | |
| 7,195,616 B2 * | 3/2007 | Diller et al. | 604/224 |
| 7,309,327 B2 | 12/2007 | Kirchhofer et al. | |
| 7,500,966 B2 | 3/2009 | Hommann | |
| 7,553,299 B2 | 6/2009 | Veasey et al. | |
| 7,686,786 B2 | 3/2010 | Moller et al. | |
| 7,811,263 B2 | 10/2010 | Burren et al. | |
| 7,828,779 B2 | 11/2010 | Kirchhofer et al. | |
| 8,096,978 B2 | 1/2012 | Markussen | |
| 8,357,120 B2 * | 1/2013 | Moller | A61M 5/14566 604/135 |
| 8,444,606 B2 | 5/2013 | Radmer et al. | |
| 8,721,601 B2 | 5/2014 | Burren et al. | |
| 8,920,383 B2 | 12/2014 | Enggaard et al. | |
| 9,775,953 B2 | 10/2017 | Enggaard et al. | |
| 2002/0120235 A1 * | 8/2002 | Enggaard | A61M 5/20 604/135 |
| 2002/0165500 A1 | 11/2002 | Bechtold et al. | |
| 2005/0033244 A1 * | 2/2005 | Veasey | A61M 5/24 604/211 |
| 2005/0261634 A1 * | 11/2005 | Karlsson | 604/197 |
| 2006/0270985 A1 | 11/2006 | Hommann et al. | |
| 2008/0208142 A1 | 8/2008 | Moller | |
| 2008/0221530 A1 | 9/2008 | Glejbol et al. | |
| 2015/0080812 A1 | 3/2015 | Enggaard et al. | |

FOREIGN PATENT DOCUMENTS

| | | |
|---|---|---|
| DE | 69810860 T2 | 11/2003 |
| DE | 10229122 A1 | 2/2004 |
| DE | 10351596 A1 | 6/2005 |
| EP | 0897728 | 2/1999 |
| EP | 897729 | 2/1999 |
| EP | 0937471 | 8/1999 |
| EP | 937476 A2 | 8/1999 |
| EP | 5016291.6 | 7/2005 |
| EP | 1909870 A1 | 4/2008 |
| JP | 2002-503116 A | 1/2002 |
| JP | 2005-508205 A | 3/2005 |
| RU | 2091087 C1 | 9/1997 |
| RU | 2212254 C2 | 9/2003 |
| SU | 1528330 A3 | 12/1989 |
| WO | WO 87/02895 | 5/1987 |
| WO | 1996/027400 A1 | 9/1996 |
| WO | 2006/114395 A1 | 8/1999 |
| WO | 9938554 | 8/1999 |
| WO | WO 01/19434 | 3/2001 |
| WO | 0195959 A1 | 12/2001 |
| WO | 02/053214 | 7/2002 |
| WO | 2002/092153 A2 | 11/2002 |
| WO | 03/011374 A1 | 2/2003 |
| WO | WO 2004/007003 | 1/2004 |
| WO | 2004/028598 A1 | 4/2004 |
| WO | 2004/030730 A2 | 4/2004 |
| WO | 04/078240 A2 | 9/2004 |
| WO | 2005018721 | 3/2005 |
| WO | 2006045526 A1 | 5/2006 |
| WO | 06/058883 | 6/2006 |
| WO | 2006076921 | 7/2006 |
| WO | 06/089768 A1 | 8/2006 |
| WO | 06/125328 A1 | 11/2006 |
| WO | 06/125329 A1 | 11/2006 |

OTHER PUBLICATIONS

Non-Final Office Action issued by the USPTO for U.S. Appl. No. 11/996,409 dated Aug. 25, 2009.
Statement by Dr. Nils Basso printed May 8, 2010.
Description of the Mechanical Components of the OPTICLIK Pen printed May 8, 2010.
Anlage E23 Eidesstattliche Versichemng Herr Peter Ryser.
Anlage E24 Eidesstattliche Versicherung Herr Nicolas Binggeli.
Anlage E25 Eidesstattliche Versichemng Frau Daniela Moser.
Offenkundige Vorbenutzung Durch Die Injektionsvorrichtung "Flexpen" E20a-c.
Anlage E26 (Fig. 10).
Notice of Opposition in EP1909870 dated Dec. 12, 2011.
English Abstract of DE202009051 Published Apr. 24, 2003.
Ypsomed AG Press Release Jan. 16, 2005 (German and English versions).
Description of the Mechanical Components of the Opticlik Pen.
Statement by Dr. Nils Basso.
Google Translation of Affidavit by Dr. Nils Basso.
Final Rejection in U.S. Appl. No. 11/996,409, filed Jan. 22, 2008 by Enggaard et al., dated Apr. 20, 2010.

* cited by examiner

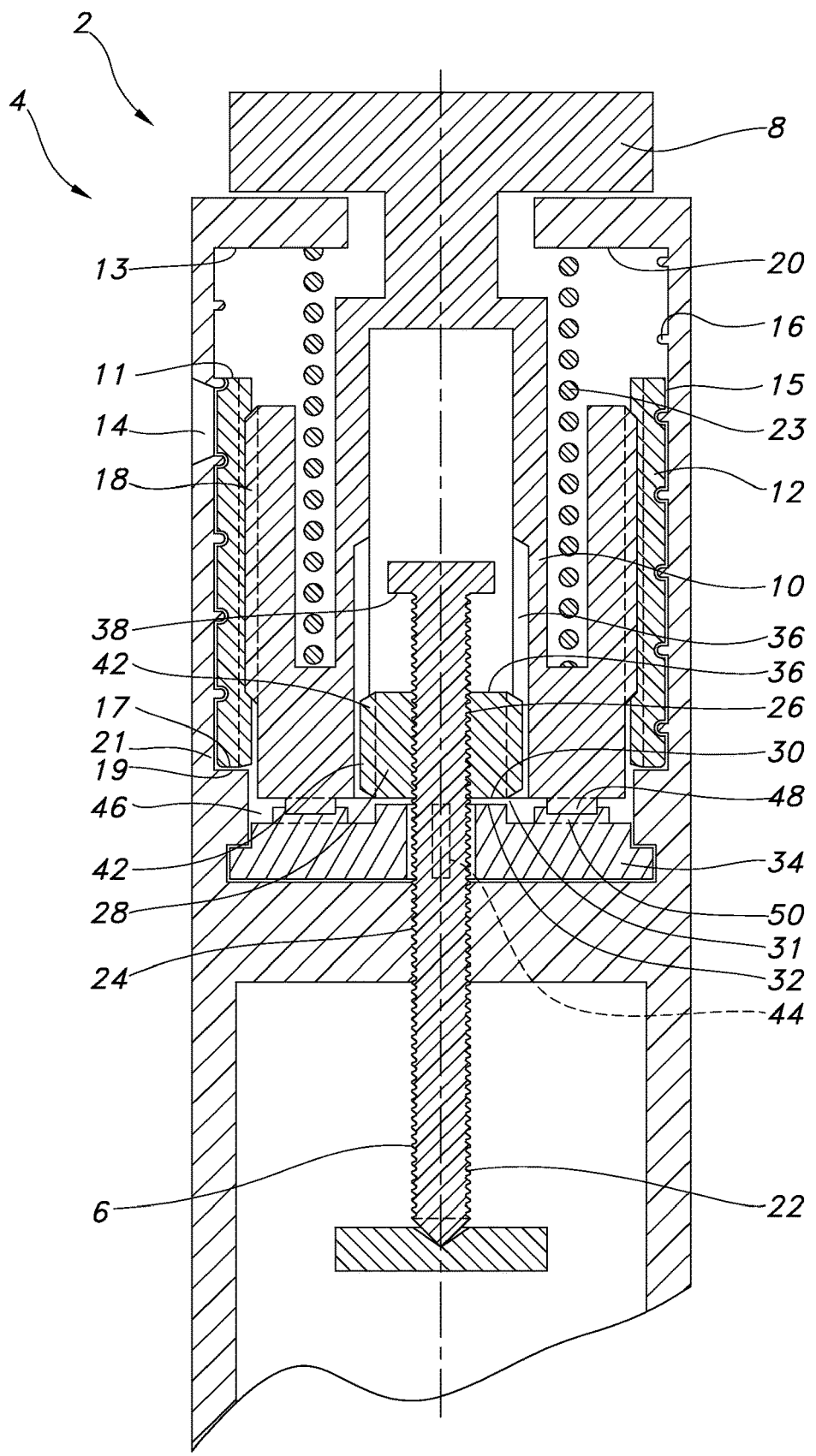

SYRINGE DEVICE WITH A DOSE LIMITING MECHANISM AND AN ADDITIONAL SAFETY MECHANISM

CROSS-REFERENCE TO RELATED APPLICATIONS

This application is a 35 U.S.C. § 371 national stage application of International Patent Application PCT/EP2006/007006 (published as WO 2007/017053), filed Jul. 17, 2006, which claimed priority of European Patent Application 05016286.6, filed Jul. 27, 2005; this application further claims priority under 35 U.S.C. § 119 of U.S. Provisional Application 60/708,211, filed Aug. 15, 2005.

FIELD OF THE INVENTION

The present invention relates to a syringe device comprising a mechanism for preventing ejection of a dose exceeding a set dose. In particular the present invention relates to a syringe device comprising two independent mechanisms for preventing ejection of a dose exceeding a set dose.

BACKGROUND OF THE INVENTION

When drugs are to be injected into the human body, it may have serious or even lethal consequences if the injected dose exceeds the set dose. Accordingly, it is important that the syringe devices comprises means for limiting ejection to the set dose.

It is an object of the present invention to provide a syringe device comprising means for prevention ejection of a dose exceeding the set dose. Furthermore, as such means may fail, it is an object of the present invention to provide a syringe device comprising a safety mechanism adapted to prevent ejection of a dose exceeding the set dose if the means for preventing fails.

SUMMARY OF THE INVENTION

The present invention relates to a syringe device for ejecting a dose of a medicament, the syringe device comprising:
  a housing,
  a dose ejecting mechanism comprising:
    a dose setting member being rotatable in relation to the housing so as to set a dose to be ejected,
    a piston rod arranged with respect to the housing such that translational movement of the piston rod in a distal direction causes the dose to be ejected,
    means for transforming translational movement of the dose setting member into translational movement of the piston rod,
  a dose limiting mechanism arranged to interact with the dose ejecting mechanism to prevent ejection of a dose exceeding the set dose, and
  a safety mechanism, which is arranged such with respect to the dose ejecting mechanism that, if the dose limiting mechanism fails, the safety mechanism prevents ejection of a dose exceeding the set dose.

An advantage of the present invention is that if a dose limiting mechanism fails to limit the ejected dose, the security mechanism is activated, and, thus, provides an extra safety for the patient.

In one embodiment the dose limiting mechanism and the safety mechanism are two independent mechanisms working independently from each other.

In one embodiment the two mechanisms are adapted to simultaneously prevent ejection of a dose exceeding the set dose. In another embodiment the safety mechanism is only activated if the dose limiting mechanism fails to prevent ejection of a dose exceeding the set dose. In one embodiment the two mechanisms are arranged such that even if the dose limiting mechanism fails, the safety mechanism is activated instantaneously such that the ejected dose does not exceed the set dose. In another embodiment the ejected dose is insignificantly larger than the set dose, if the dose limiting mechanism fails and the safety mechanism is activated. By insignificantly larger is meant that the change in dose is too small to have serious or fatal consequences.

The housing may define a passage for the piston rod, the passage may have a threaded inner surface for engagement with a threaded outer surface of the piston rod, the piston rod may be arranged with respect to the housing such that rotation of the piston rod relative to the housing causes the piston rod to be displaced translationally relative to the housing.

In one embodiment at least one of the dose limiting mechanism and the safety mechanism is adapted to limit relative rotational movement between the piston rod and the housing, to a rotation corresponding to ejection of the set dose. This may be the case, when the piston rod comprises a threaded outer surface adapted to engage a threaded inner surface of the housing. Accordingly, rotational locking of the piston rod (relative to the housing) results in a translational locking of the piston rod relative to the housing.

The dose limiting mechanism may comprise at least one first stopping surface adapted to engage at least one corresponding second stopping surface of the housing. Furthermore, rotation of the dose setting member during dose setting may cause the first stopping surface to move away from the second stopping surface and rotation during dose ejection may cause the first and the second surface(s) to move towards each other. Furthermore, ejection of a dose may be prevented when the first stopping surface abut the second stopping surface. The dose setting member may comprise the at least one first stopping surface. Alternatively, or as a supplement, the dose setting member may be coupled to a cylinder comprising a first stopping surface, and said cylinder may be adapted to indicate the set dose. The first and second stopping surfaces may be substantially plane surfaces which may extend in a direction parallel with the axial direction of the syringe device. Alternatively, the stopping surfaces may extend in a plane transverse to the axial direction, such as a plane orthogonal to the axial direction.

In one embodiment the safety mechanism comprises: a limiter defining a passage for the piston rod, the passage of the limiter defining a threaded inner surface for engagement with the threaded outer surface of the piston rod, and a driver defining a passage for the limiter, the driver being rotationally retained in relation to the limiter, the driver being coupled to the dose setting member such that rotation of the dose setting member during dose setting causes the driver to rotate, wherein relative rotation between the drive and the piston rod during dose setting causes the limiter to move away from a stopping position wherein the limiter prevents ejection of a dose.

In one embodiment the syringe device is adapted to prevent setting of a dose which exceeds the amount of a medicament in a reservoir of the syringe device. In such embodiments, the piston rod may comprise an end-of-dose stopping surface adapted engage a corresponding surface of the limiter, when the set dose corresponds to the amount of the medicament in the reservoir of the device. Accordingly, in such embodiments the limiter serves two functions, a first function being prevention of setting of a dose exceeding the amount of the medicament left in the reservoir and a second function being a security function adapted to prevent ejection of a dose exceeding the set dose.

Moreover, the syringe device may comprise an ejection assisting system for providing an ejection force for assisting an operator of the device in forcing the piston in said distal direction so as to eject the set dose. The ejection assisting system may be adapted to force the piston in the distal direction so as to eject the dose, without the aid of the user, when the user has initiated the ejection.

The ejection assisting system may comprise a spring, such as a torsional spring which is arranged to rotate the driver relative to the housing. The spring may be pre-strained when limiter is in the stopping position. Especially when the spring is pre-strained, the redundant security system of the present invention is advantageous, as accidental un-straining of the pre-strained spring, may cause the piston rod to rotate (and thus move translationally) corresponding to a lethal dose, such as 100 IU of insulin.

DESCRIPTION OF THE DRAWINGS

The invention will now be described in further detail with reference to FIG. 1, which discloses a syringe device according to the present invention.

FIG. 1 shows a syringe device 2 comprising a housing 4 and a piston rod 6. The syringe device 2 also comprises a dose setting member 8 and a driver 10, which in the FIGURE are combined into one single unit. The syringe device further comprises a scale drum 12 for indicating a set dose through a window 14. The scale drum 12 has a threaded outer surface 15 adapted to engage a corresponding threaded inner surface 16 of the housing. The scale drum 12 is rotationally retained relative to the driver 10 through a grove-tongue engagement 18. The drum scale 12 comprises a first stopping surface 17 adapted to engage a second stopping surface 19 of the housing. The first stopping surface 17 and the second stopping surface 19 constitutes the dose limiting mechanism 21. The first stopping surface is moved away from the second stopping surface 19 during dose setting and towards each other during dose ejecting. When the two surfaces abut each other, the device is prevented from ejecting the medicament.

FIG. 1 further shows an example of a dose setting member 8 rotatable and longitudinally fixed in relation to the housing 4 so as to set a dose to be injected.

The syringe device comprises an ejection assisting system in the form of a pre-strained torsional spring 23 extending between the driver 10 and a proximal part 20 of the housing. Accordingly, when the dose setting member 8 is rotated to set a dose, the spring is strained even further.

The piston rod 6 comprises a threaded outer surface 22 adapted to engage a corresponding threaded inner surface of the housing 24 and accordingly rotation of the piston rod relative to the housing causes the piston rod to move translationally in relation to the housing. The threaded outer surface 22 of the piston rod also engages a threaded inner surface 26 of a limiter 28, which in FIG. 1 is positioned in a stopping position wherein a bottom surface 30 of the limiter engages an upper surface 32 of a piston rod guide 34. The bottom surface 30 and the upper surface 32 constitute the safety mechanism 31. An air gap may be provided between the bottom surface 30 and the upper surface 32 which allows the limiter and the piston rod to rotate an angel corresponding an insignificant increase in the injected dose e.g. 3 IU of insulin, if the dose limiting mechanism 21 fails during dose injection.

Moreover, an upper end-of-content surface 36 of the limiter 28 is adapted to engage a lower end-of-content surface 38 of a T-shaped end part 40 of the piston rod. The end-of-content surfaces are adapted to engage, when the set dose corresponds to the amount of a medicament remaining in a reservoir (not shown) of the device. Accordingly, the engagement of the end-of-content surfaces prevents setting of a dose exceeding the amount of a medicament remaining in the reservoir. It will be appreciated that the distance between the end-of-content surfaces thus corresponds to the amount of the medicament remaining in the reservoir.

Moreover, an upper surface 11 of the drum 12 may be adapted to engage a lower surface 13 of the housing, when the maximum dose is set. The maximum dose is the largest dose which may be set for each ejection (provided that the syringe device comprises the required amount of medicament). The maximum dose does not correspond to the end-of-content dose which relates the remaining amount of a medicament in the device. Accordingly, as long as the remaining amount of medicament in the device is larger than the maximum dose, the end-of-content surfaces will not abut each other during dose setting, whereas when the remaining amount of medicament in the device is lower than the maximum dose, the maximum dose surfaces will not abut each other during dose setting, as the end-of-content surfaces prevents further rotation.

The limiter 28 and the driver 10 are locked for relative rotation by means of grove-tongue engagement 42. Thus, when the piston rod is locked for rotation relative to the housing, a relative rotation between the driver 8 and the piston rod 6 causes the limiter to move away from the stopping position and towards the t-shaped end part 40 (i.e. upwards in the FIGURE). The piston rod is locked for rotation relative to the housing when the piston rod guide 34 is locked for rotation relative to the housing (not shown), as the piston rod guide 34 and the piston rod are locked for relative rotation due to the grove-tongue engagement 44.

The driver 12 and the piston rod guide 34 are interconnected by a two-way ratchet mechanism 46 comprising at least one first retaining member 48 defined by the driver 12 and at least one second retaining member 50 defined by the piston rod guide 34. The two-way ratchet mechanism is adapted to allow relative rotational movement between the driver 12 and the piston rod guide 34 during dose setting and to ensure that rotational movement of the driver during dose ejection is transferred to the piston rod guide 34.

The use of the device is as follows. Initially the piston rod guide is locked for rotation relative to the housing. Then the dose setting member is rotated, which causes the driver and the drum scale to rotate and the pre-strained spring to be strained even further. At the same time the limiter moves towards the T-shaped end part. If the user tries to set a dose exceeding the amount of medicament in the device, the limiter abuts the T-shaped end part whereby an even larger dose cannot be set. The dose is ejected by removing the rotational lock between the piston rod guide 34 and the housing whereby the strained spring forces the driver to rotate. The rotating driver forces the piston rod guide to rotate which again forces the piston rod to rotate. Due to the grove-tongue engagement 44 and the threaded interconnection between the piston rod and the housing, the rotating piston rod is forced to move forward and thus the medicament is expelled from the device.

The invention claimed is:

1. A syringe device for ejecting a dose of a medicament, the syringe device comprising:
   a housing;
   a dose setting member rotatable and longitudinally fixed in relation to the housing so as to set a dose to be ejected,
   a dose ejecting mechanism comprising:
      a piston rod arranged with respect to the housing such that translational movement of the piston rod in a distal direction causes the set dose to be ejected,
      structure for transforming rotational movement of the dose setting member into translational movement of the piston rod during ejection of the set dose in the form of an ejection assisting system comprising a pre-strained torsional spring arranged to rotate a driver relative to the housing, the pre-strained torsional spring providing an ejection force forcing the piston rod in the distal direction so as to eject the set dose without the aid of a user, when the user has initiated the ejection of the set dose;
   a dose limiting mechanism operably connected with the dose ejecting mechanism to prevent ejection of a dose exceeding the set dose; and
   a safety mechanism structure operably connected to the dose ejecting mechanism such that if the dose limiting mechanism fails, the safety mechanism structure prevents ejection of a dose exceeding the set dose.

2. A syringe device according to claim 1, wherein the housing defines a passage for the piston rod, the passage having a threaded inner surface for engagement with a threaded outer surface of the piston rod, the piston rod being arranged with respect to the housing such that rotation of the piston rod relative to the housing causes the piston rod to be displaced translationally relative to the housing.

3. A syringe device according to claim 1, wherein at least one of the dose limiting mechanism and the safety mechanism structure is adapted to limit relative rotational movement between the piston rod and the housing, to a rotation corresponding to ejection of the set dose.

4. A syringe device according to claim 1, wherein the dose limiting mechanism comprises a first stopping surface adapted to engage a corresponding second stopping surface of the housing, and wherein rotation of the dose setting member during dose setting causes the first stopping surface to move away from the second stopping surface and wherein ejection of a dose is prevented when the first stopping surface abuts the second stopping surface.

5. A syringe device according to claim 4, wherein the dose setting member comprises the first stopping surface.

6. A syringe device according to claim 4, wherein the dose setting member is coupled to a cylinder comprising the first stopping surface, said cylinder being adapted to indicate the set dose.

7. A syringe device according to claim 1, wherein the safety mechanism structure comprises:
   a limiter defining a passage for the piston rod, the passage of the limiter defining a threaded inner surface for engagement with a threaded outer surface of the piston rod; and
   the driver defining a passage for the limiter, the driver being rotationally retained in relation to the limiter, the driver being coupled to the dose setting member such that rotation of the dose setting member during dose setting causes the driver to rotate;
wherein relative rotation between the driver and the piston rod during dose setting causes the limiter to move away from a stopping position wherein the limiter prevents ejection of a dose exceeding the set dose.

8. A syringe device according to claim 1, wherein the torsional spring is prestrained when the dose limiting mechanism is in a stopping position.

* * * * *